(12) United States Patent
Primous et al.

(10) Patent No.: US 9,357,620 B2
(45) Date of Patent: May 31, 2016

(54) OCCUPANCY SENSOR WITH DIMMER FEATURE AND NIGHT LIGHT AND METHOD OF LIGHTING CONTROL USING THE SAME

(71) Applicant: Hubbell Incorporated, Shelton, CT (US)

(72) Inventors: Christopher C. Primous, Greer, SC (US); Thomas J. Batko, Wallingford, CT (US)

(73) Assignee: Hubbell Incorporated, Shelton, CT (US)

( * ) Notice: Subject to any disclaimer, the term of this patent is extended or adjusted under 35 U.S.C. 154(b) by 0 days.

(21) Appl. No.: 14/620,938

(22) Filed: Feb. 12, 2015

(65) Prior Publication Data

US 2015/0156852 A1 Jun. 4, 2015

Related U.S. Application Data

(63) Continuation of application No. 11/529,709, filed on Sep. 29, 2006, now Pat. No. 8,970,372.

(51) Int. Cl.
| | | |
|---|---|---|
| *G08B 13/00* | (2006.01) | |
| *H05B 37/02* | (2006.01) | |
| *A61F 2/46* | (2006.01) | |
| *H05B 33/08* | (2006.01) | |

(52) U.S. Cl.
CPC .......... *H05B 37/0227* (2013.01); *A61F 2/4611* (2013.01); *H05B 33/0854* (2013.01); *H05B 37/0218* (2013.01); *H05B 37/0281* (2013.01); *Y02B 20/42* (2013.01); *Y02B 20/46* (2013.01)

(58) Field of Classification Search
CPC .............. A61F 2/4611; H05B 33/0854; H05B 37/0218; H05B 37/0227; H05B 37/0281; Y02B 20/42; Y02B 20/46
See application file for complete search history.

(56) References Cited

U.S. PATENT DOCUMENTS

| | | | |
|---|---|---|---|
| 3,500,455 A | 3/1970 | Ross et al. | |
| 3,898,383 A | 8/1975 | Herbits | |
| 4,225,808 A | 9/1980 | Saraceni | |
| 4,233,545 A | 11/1980 | Webster et al. | |
| 4,344,071 A | 8/1982 | Allen | |
| 4,540,984 A | 9/1985 | Waldman | |
| 4,751,399 A | 6/1988 | Koehring et al. | |
| 5,189,393 A | 2/1993 | Hu | |
| 5,216,333 A | 6/1993 | Nuckolls et al. | |
| 5,357,170 A | 10/1994 | Luchaco et al. | |
| 5,406,173 A * | 4/1995 | Mix | H05B 37/02 315/156 |

(Continued)

FOREIGN PATENT DOCUMENTS

| | | |
|---|---|---|
| EP | 0669786 A1 | 8/1995 |
| WO | 8500264 A1 | 1/1985 |

*Primary Examiner* — Ojiako Nwugo
(74) *Attorney, Agent, or Firm* — Dickinson Wright PLLC

(57) ABSTRACT

System and method are provided where an occupancy sensor with a time delay function designed to dim the lights, for example as a warning, after a first period of time has expired without detecting room occupancy. The lights remain dimmed for a second period of time, and then are turned off after a third period of time has expired without detecting room occupancy. If occupancy is detected during the first period of time, the lights will remain on. If occupancy is detected during the second or third period of time, the lights will be turned on to, for example, previous brightness. A night light can be added to, and/or incorporated in, an occupancy sensor which includes the dimmer feature.

20 Claims, 14 Drawing Sheets

(56) References Cited

U.S. PATENT DOCUMENTS

| | | | |
|---|---|---|---|
| 5,489,827 A * | 2/1996 | Xia | H05B 37/0227 315/154 |
| 5,598,066 A | 1/1997 | Wiesemann et al. | |
| 5,699,243 A | 12/1997 | Eckel | |
| 5,747,937 A | 5/1998 | Wiesemann et al. | |
| 6,151,529 A | 11/2000 | Batko | |
| RE37,135 E | 4/2001 | Elwell | |
| 6,259,351 B1 | 7/2001 | Radosavljevic et al. | |
| 6,275,163 B1 | 8/2001 | Bogorad et al. | |
| 6,555,966 B2 | 4/2003 | Pitigoi-Aron et al. | |
| 6,614,013 B2 | 9/2003 | Pitigoi-Aron et al. | |
| 6,617,560 B2 | 9/2003 | Forke | |
| 6,888,323 B1 | 5/2005 | Null | |
| 6,933,486 B2 | 8/2005 | Pitigoi-Aron et al. | |
| 6,940,230 B2 | 9/2005 | Myron et al. | |
| 7,268,682 B2 * | 9/2007 | Bialecki, Jr. | H05B 37/0227 315/149 |
| 7,271,543 B1 * | 9/2007 | Goldstein | H05B 37/02 315/153 |
| 7,339,471 B1 * | 3/2008 | Chan | G08B 15/002 315/159 |
| 7,405,671 B2 | 7/2008 | Sebescak | |
| 7,511,613 B2 * | 3/2009 | Wang | H05B 37/0227 340/539.1 |
| 7,733,224 B2 * | 6/2010 | Tran | G06F 19/3418 340/3.1 |
| 8,064,412 B2 * | 11/2011 | Petite | H04L 12/2825 340/540 |
| 2002/0179817 A1 | 12/2002 | Pitigoi-Aron et al. | |
| 2003/0197113 A1 | 10/2003 | Pitigoi-Aron et al. | |
| 2004/0163118 A1 * | 8/2004 | Mottur | H04N 5/23203 725/105 |
| 2005/0047133 A1 | 3/2005 | Pitigoi-Aron et al. | |
| 2005/0185392 A1 * | 8/2005 | Walter | A61L 9/037 362/96 |
| 2005/0258954 A1 * | 11/2005 | Ruskin | F21V 23/0442 340/527 |
| 2005/0265050 A1 | 12/2005 | Miller | |
| 2006/0245174 A1 * | 11/2006 | Ashdown | H05B 33/0818 362/85 |
| 2006/0250745 A1 * | 11/2006 | Butler | H05B 37/0281 361/160 |
| 2006/0262521 A1 * | 11/2006 | Piepgras | E04B 9/006 362/149 |
| 2007/0014119 A1 * | 1/2007 | Burkett | B60Q 1/1423 362/459 |

* cited by examiner

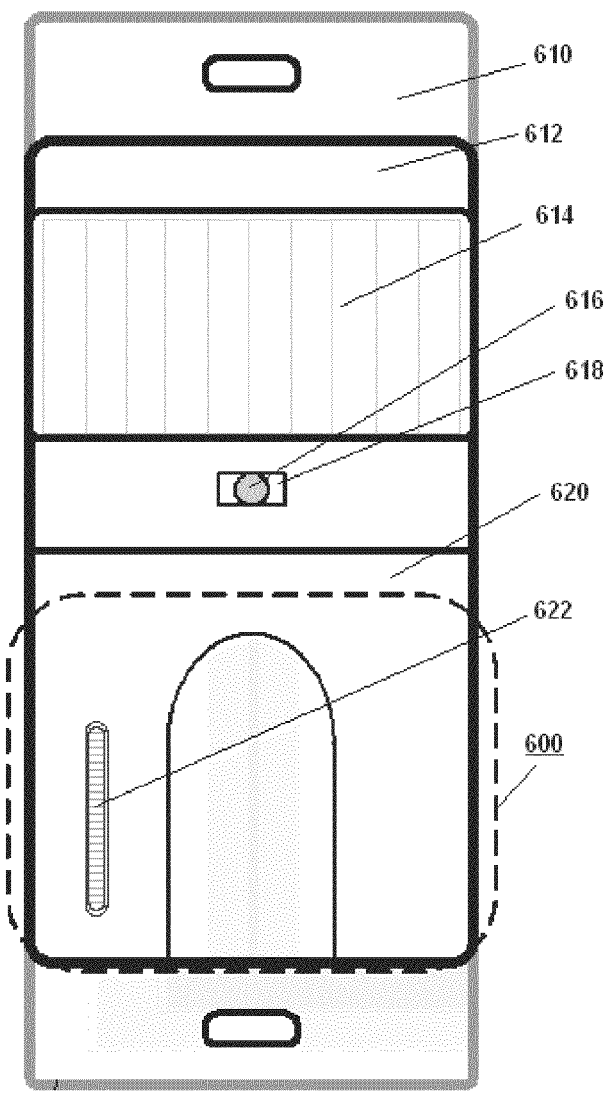
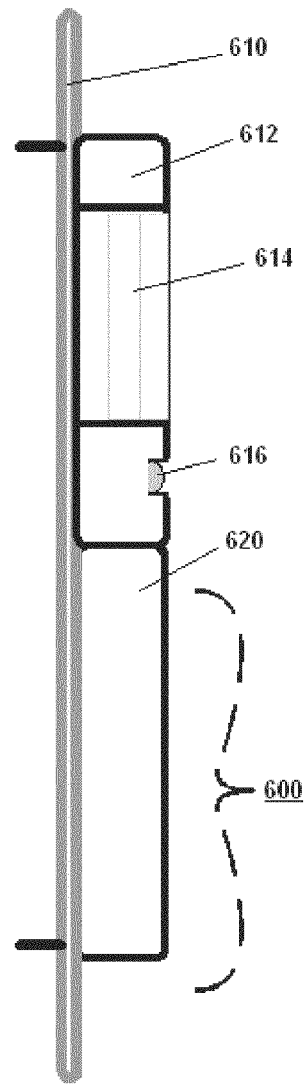
FIG. 6A
FIG. 6B
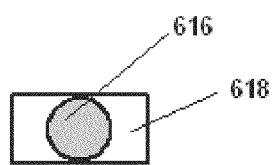
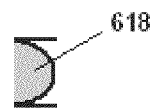
FIG. 6C
FIG. 6D

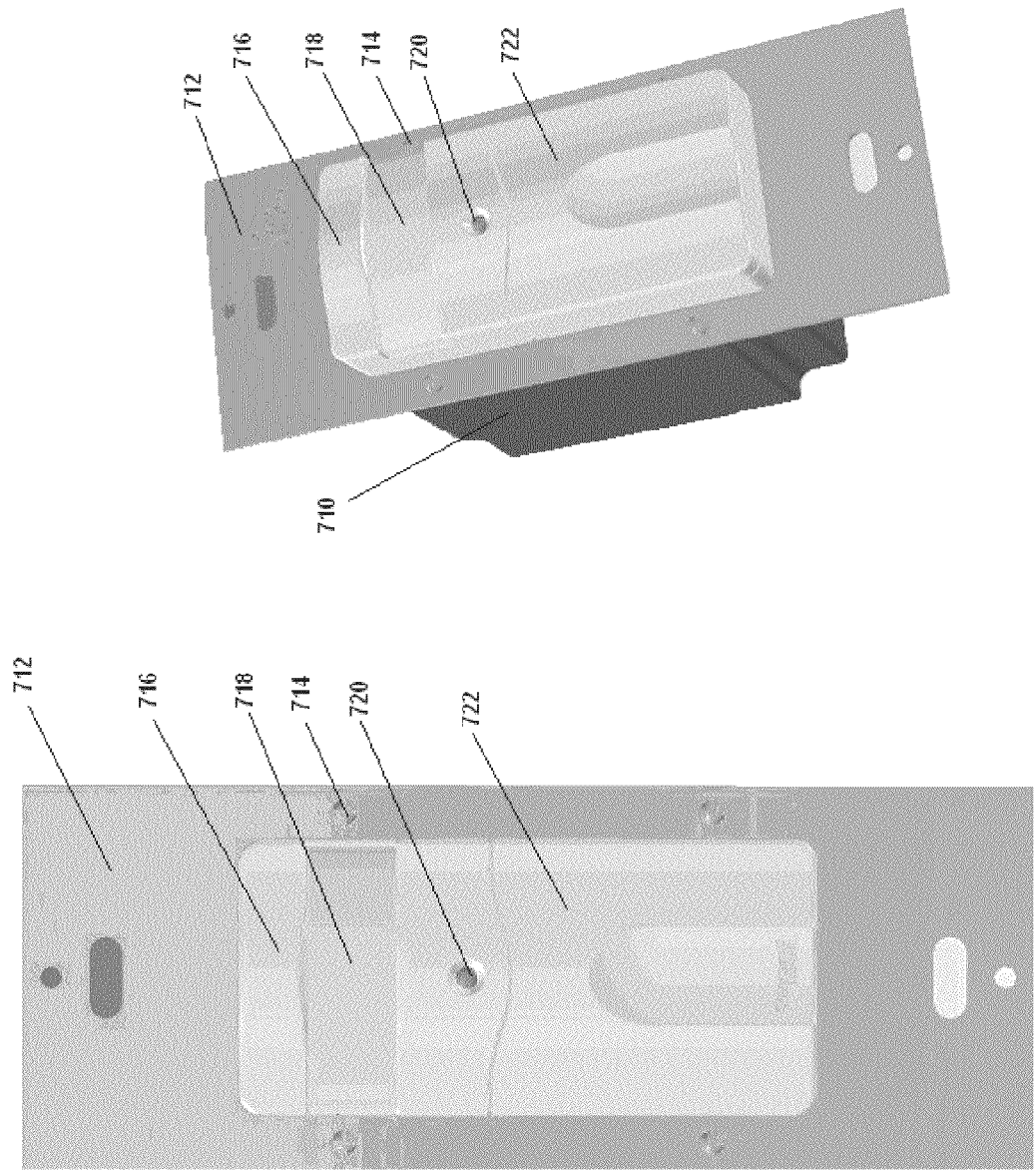

OCCUPANCY SENSOR WITH DIMMER FEATURE AND NIGHT LIGHT AND METHOD OF LIGHTING CONTROL USING THE SAME

CROSS-REFERENCE TO RELATED APPLICATIONS

The present application is a continuation of U.S. patent application Ser. No. 11/529,709, filed Sep. 29, 2006, the entire content of which is incorporated by reference herein.

BACKGROUND OF THE INVENTION

1. Field of the Invention

The present invention generally relates to systems and methods for controlling room lighting where an occupancy sensor controls room lighting using standard infrared and/or motion sensor techniques. More particularly, the present invention relates to lighting systems and methods for controlling lighting in an area based on occupancy detection, and dimming features associated with reducing and/or increasing the level of lighting in the area such that a warning can be provided to room occupants when the level of lighting in the room is about to change based on occupancy detection.

2. Discussion of the Background

Conventional light management system for controlling a load circuit where a motion sensor is configured to automatically control the load circuit and/or the night light based on detected motion is disclosed in, for example, U.S. Pat. No. 6,888,323 to Null et al., the entire disclosure of which is hereby incorporated by reference. As described in U.S. Pat. No. 6,888,323 to Null et al., a light management system includes a manual wall switch for manually operating a room light. As shown in FIGS. 2-4 thereof, night light unit provides reduced or low level room lighting when the room light is off. A motion sensor adjusts room light and/or the night light unit based on a detected occupancy of the room. A light sensor unit detects a level of room lighting and adjusting the room light and/or night light unit based on a level of detected room lighting. The manual switch, the night light unit, the motion sensor unit and the light sensor unit 205 are integrated to operate collectively. As shown in a flow chart of FIG. 5, motion in a room is monitored to determine if a room is occupied, and if the room is not occupied and the light is not on then the system continues to monitor for motion in the room. On the other hand, if the room is not occupied and the room light is on, then the room lighting is lowered or reduced by turning off the room light, dimming the room light, turning the night light off, dimming the night light or a combination thereof. Alternatively, or in addition to reducing the level of light emitted from the room light, the level of light emitted from the night light is also increased. If the room is occupied, room lighting conditions are assessed by the light sensor, and if the system determines that there is an insufficient level of room lighting, then the level of room lighting is increased by increasing the amount of light that is emitted by the room light and/or the night light. Alternatively, or in addition to increasing the level of light emitted from the room light, the level of light emitted from the night light is also decreased. The level of light emitted by the night light is integrally associated with the level of light emitted by the room light such that the night light and the room light work together to ensure adequate lighting in the room.

Another conventional device for controlling the level of light in a room as a function of sensed occupancy and ambient light is disclosed in U.S. Pat. No. 5,406,173 to Mix et al., the entire disclosure of which is hereby incorporated by reference. The device described in U.S. Pat. No. 5,406,173 to Mix et al., as shown in FIG. 1 thereof, includes a sensor that detects whether the room is occupied, a timing circuit that detects the duration of time that the room is occupied and unoccupied, a light meter that detects the level of ambient light entering the room, and control circuitry that controls the lights in the room in response to the sensor and light meter. As shown in FIG. 4, this device has three modes of operation: (1) when the room is occupied, it is determined whether the brightness output by lighting unit should be increase or decreased based on increases or decreases of ambient light detected by light meter; (2) when the room is unoccupied for a brief period of time, light control circuit 120 freely adjusts the brightness created by lighting unit 150 up and down to compensate for increases or decreases in the measured ambient light level; and (3) when the room has been unoccupied for a substantial time period, light control unit turns the lighting unit off to remain off until occupancy detector detects the presence of a person in the room again sending a signal to the light control circuit which switches the lighting unit on at the light level determined by light level adjustor.

U.S. Pat. No. 6, 275,163 to Bogorad et al., the entire disclosure of which is hereby incorporated by reference, discloses a conventional occupancy sensor which is combined with an automatic dimmer to control the on/off state of a lamp and its level of brightness. According to U.S. Pat. No. 6, 275,163 to Bogorad et al., automatic switch/dimmer includes an occupancy sensor which provides line output to a microprocessor logic device, which is connected to a key or a present control. As shown in FIG. 3 of U.S. Pat. No. 6, 275,163 to Bogorad et al., the output of the microprocessor logic device is fed to a dimmer module which turns the lamp on or off or can be stepped down from maximum light output to minimum brightness. According to operation flowchart of FIG. 1 of U.S. Pat. No. 6, 275,163 to Bogorad et al., the operation of its automatic switch/dimmer is described as follows. At the start of operation, automatic switch/dimmer device is in attention state, that is monitoring motion while the lamp is off. If no motion is detected, a signal is generated to command the switch/dimmer to maintain the present condition. If motion is detected, a signal is generated to turn the lamps on and increase the brightness level towards maximum brightness. If a the key is not operated, then the lamp goes to maximum brightness. If a key has been activated, a signal is generated to control the lamp brightening to stop at the key setting, whereby the lamp remains on, and the device returns to the attention state. If motion is detected, a signal is generated to retain the lamp at the level selected. This operation will continue as long as motion is detected. If motion is not detected, a signal is generated to cause the lamp to slowly dim. If no motion is further detected, a signal is generated to place the device in its attention state. If motion is detected, then a signal is generated to cause the lamp to go on to its previously selected brightness, and the sensor returns to its attention state.

U.S. Pat. No. 5,489,827 to Xia, the entire disclosure of which is hereby incorporated by reference, discloses a system for controlling the intensity of a lamp including a remote sensing device, which is separate from the light controller and independent of a utility power line, for detecting the presence of an occupant within an area. This patent discloses the use of a remote dimming controller for remotely adjusting the illumination level of a light fixture, such that in the absence of an occupancy signal received from the transmitter within a "second" predetermined period of time (for example, about 12 minutes), the controller automatically reduces the level of illumination produced by the lamp to the lowest non-zero illumination level. When no occupancy signal is received within a "third" predetermined period of time (for example, about 90 minutes), the light controller controls turning off power to the lamp.

None of the prior art systems provide any warning, for example to persons who may still occupy the room, that the level of lighting in the room is about to change based on, for example, the lack of motion detected by the occupancy sensor.

SUMMARY OF THE INVENTION

Exemplary embodiments of the present invention address at least the above problems and/or disadvantages and provide at least the advantages described below. Accordingly, an aspect of the present invention is to provide a.

Exemplary embodiments of the present invention provide a system and method where an occupancy sensor with a time delay function designed to dim the lights, for example as a warning, after a first period of time has expired without detecting room occupancy. The lights remain dimmed for a second period of time, and then are turned off after a third period of time has expired without detecting room occupancy. If occupancy is detected during the first period of time, the lights will remain on. If occupancy is detected during the second or third period of time, the lights will be turned on to, for example, previous brightness.

In an exemplary implementations of certain embodiments of the present invention, the first, second and third time periods can be varied and/or preset, and the light level (brightness) before, after and during the dimming can also be preset and/or varied.

In yet another exemplary implementation, the level of brightness when the lights are dimmed, for example during the second time period, is fixed to be approximately one half the level of brightness when the lights were on during, for example, the first time period.

According to other exemplary embodiments of the present invention, a night light can be added to, and/or incorporated in, an occupancy sensor which includes the dimmer feature.

In an exemplary implementation of the present invention, the night light is a light emitting diode (LED) which is positioned behind a passive infra red (PIR) lens of an occupancy sensor to illuminate the lens area when the lights are off, that is, when the sensor's load is off.

In yet another exemplary implementation of the present invention, the LED can also be mounted through the housing of an occupancy sensor to provide a more direct light.

LED of any color can be implemented to provide the night light.

In yet another exemplary implementation, a photocell can be added to detect ambient light so that the LED is activated only if there is insufficient ambient light.

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawings, wherein:

FIGS. 6A-6D are diagrams of perspective views of an occupancy sensor and indicator LED according to an exemplary implementation of certain embodiments of the present invention.

FIGS. 7A-7D illustrate an occupancy sensor according to another exemplary implementation of certain embodiments of the present invention.

DETAILED DESCRIPTION OF EXEMPLARY EMBODIMENTS

Figure 1A:
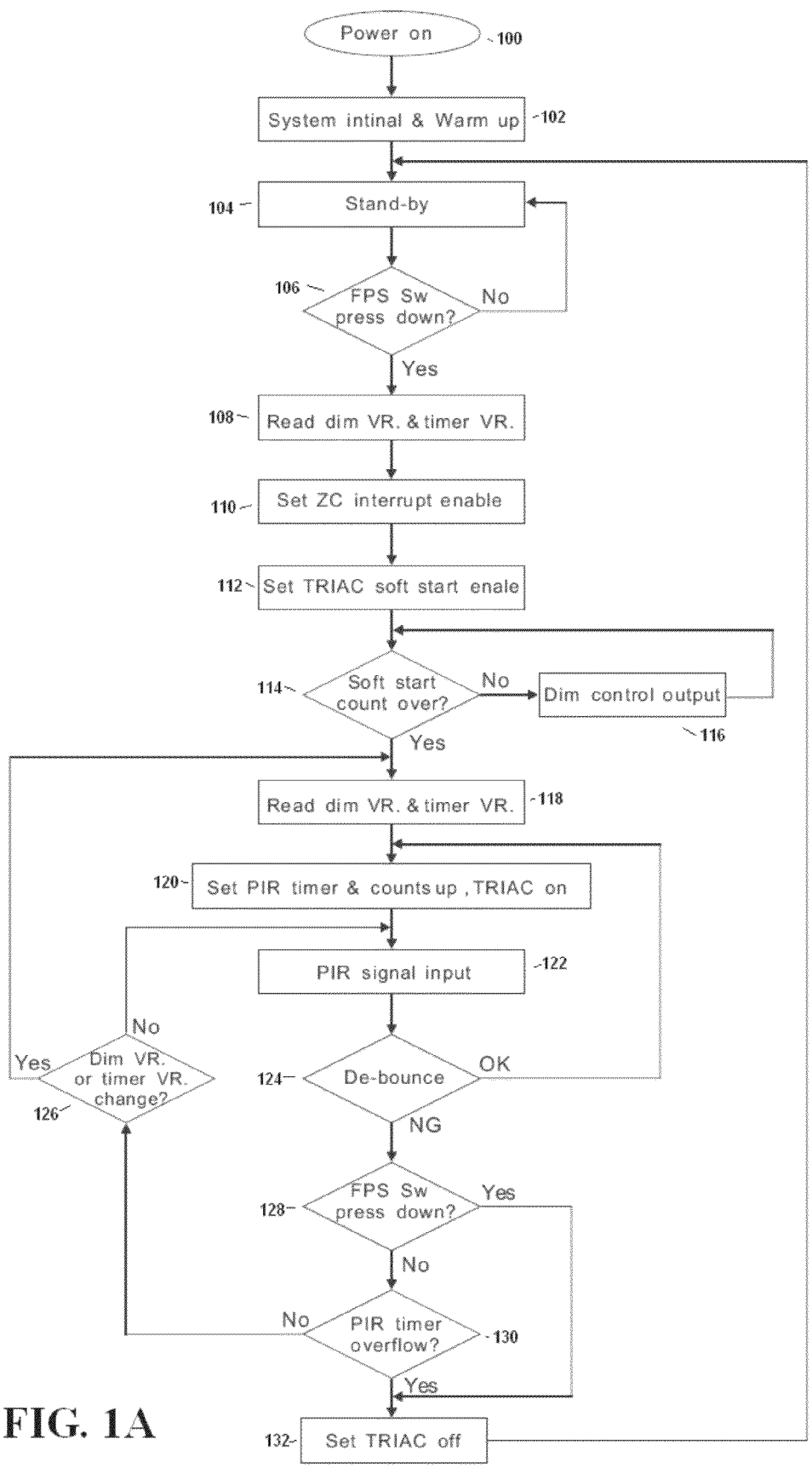
FIG. 1A shows an operational flowchart of system according to an exemplary embodiment of the present invention.

Referring now to the drawings, wherein like reference numerals designate identical or corresponding parts throughout the several views, embodiments of the present invention are shown in schematic detail.

The matters defined in the description such as a detailed construction and elements are nothing but the ones provided to assist in a comprehensive understanding of the invention. Accordingly, those of ordinary skill in the art will recognize that various changes and modifications of the embodiments described herein can be made without departing from the scope and spirit of the invention. Also, well-known functions or constructions are omitted for clarity and conciseness.

At the outset, it is noted that exemplary embodiments of the present inventions are applicable to, and may share certain features with, occupancy sensors disclosed in U.S. Pat. Nos. 6,151,529 and 5,699,243, and the entire disclosures of both of these patents are hereby incorporated by reference.

According to exemplary embodiment of the present invention, a system and method are provided where an occupancy sensor with a time delay function is designed to dim the lights, for example as a warning, after a first period of time has expired without detecting room occupancy. The lights remain dimmed for a second period of time, and then are turned off after a third period of time has expired without detecting room occupancy. If occupancy is detected during the first period of time, the lights will remain on. If occupancy is detected during the second or third period of time, the lights will be turned on to, for example, previous brightness.

In an exemplary implementation, once the time delay feature of an occupancy sensor has reached the end of its cycle, the lights controlled by the switch will dim to a warn the room occupants that the lighting fixtures are about to be turned off. Once motion is detected again by the device the lighting fixtures controlled by the device will return to full brightness.

Figure 5B:
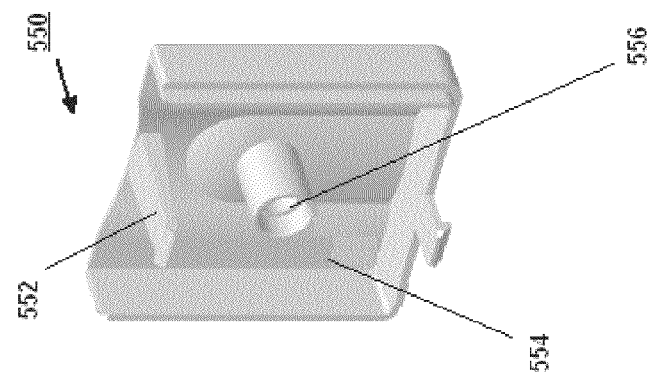
FIGS. 5A and 5B illustrate an occupancy sensor according to an exemplary implementation of certain embodiments of the present invention.
Figure 5A:
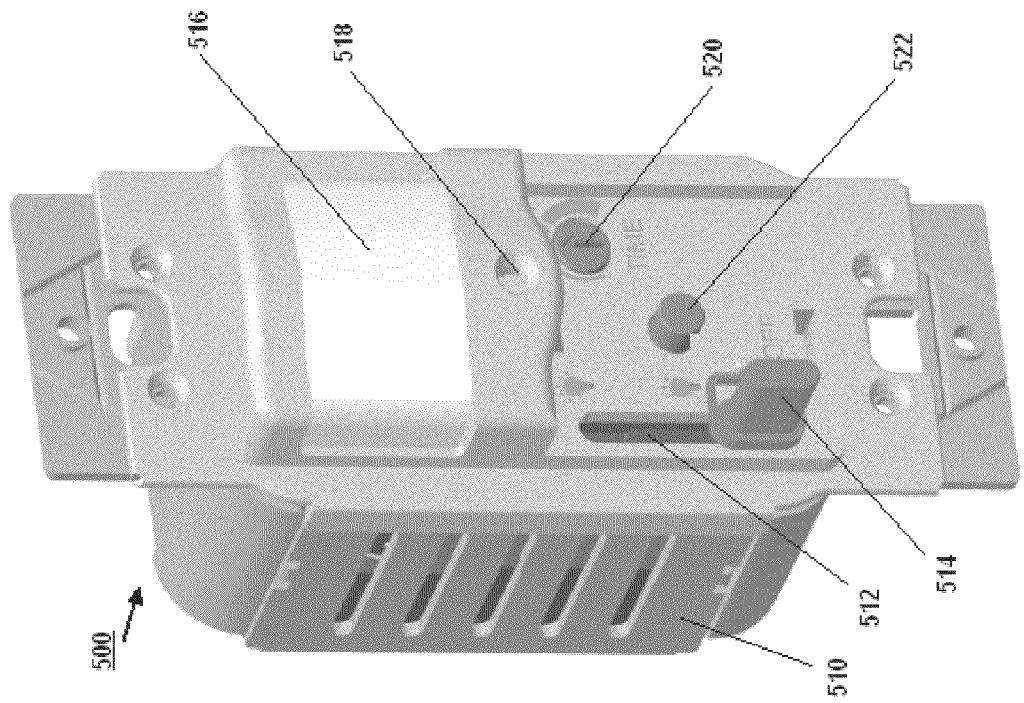
Figure 7B:
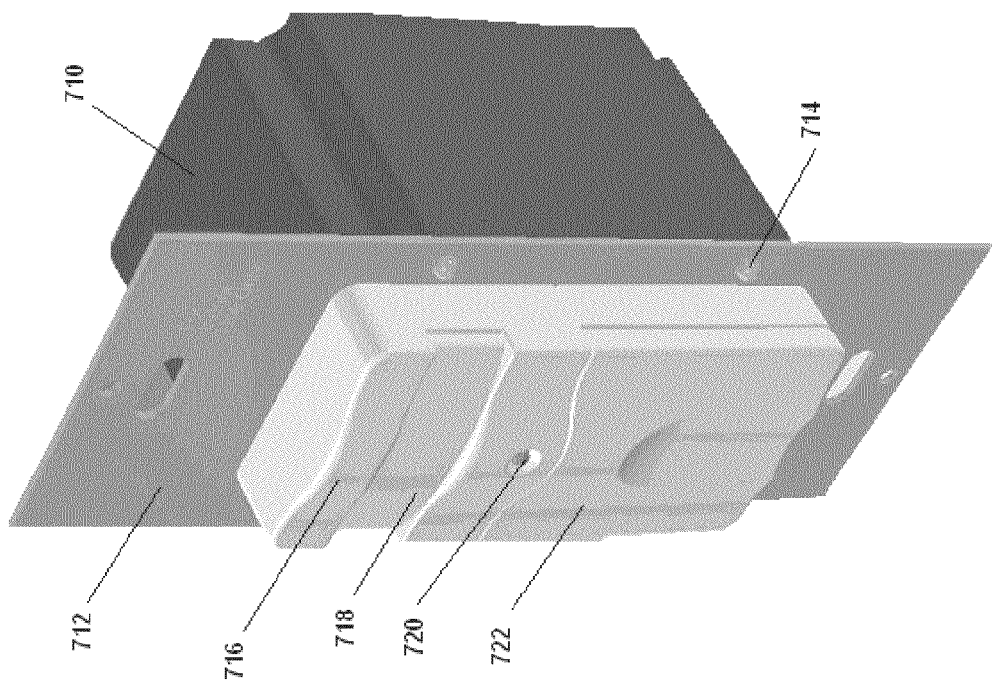
Figure 7A:
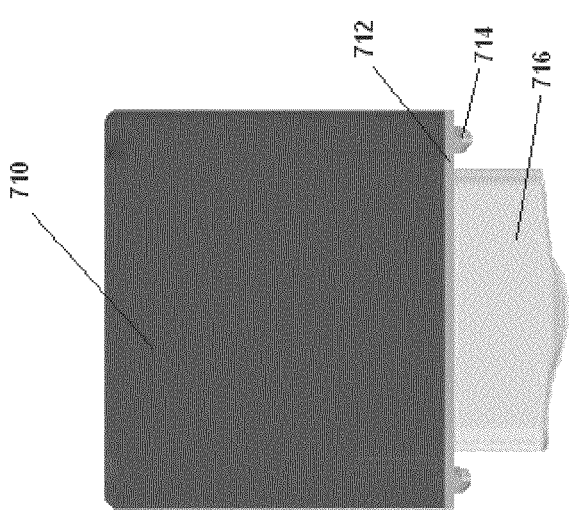

An example of a wall mounted passive infrared occupancy sensor in accordance with an embodiment of the present invention is illustrates in FIGS. 5A and 5B where an occupancy sensor 500 comprises housing 510, passive infrared (PIR) lens 516 and a front press switch (FPS) 550 which can be used to manually switch lights on and off. A dimming control and airgap switch are provided and operated by means of a front mounted slide pot 514 which slides in the housing opening 512 to allow performing manual dimming function for providing variable output lighting level. A timer 520 is provided to provide a manually adjustable time out for sensor 500. An occupancy detection indicator can be provided by means of an LED 518. FPS 500 can be implemented to have a contoured main body 554 and protruding receptacle 556 that removably engages cylindrical switch 522. Clips 552 can be provided for additional stability and engagement with corresponding recesses (shown, but not labeled) in the front portion of occupancy sensor 500.

In an exemplary implementation, the light level can be continuously variable between 10% and 100% of full brightness. The 10% lighting level can be the designed minimum lower limit to prevent wasted power (that is, the lights set where the lamp's filament will not be visible but powered).

In an exemplary implementation, the sensor is configured to dim the light to 50% of current brightness level when a certain preset time (for example, 60 seconds) a pending before for the lights are switched off to warn occupants that the lights are about to switch off. If occupant is sensed (for example occupant responds to the warning by a movement), the time delay is reset back to the original delay set by the time out adjustment (for example, by time out sensor 500 of FIG. 5A).

In an exemplary implementation, a soft start feature is provided whereby a delay (for example, a slight delay) occurs before the lights are turned on to full current brightness. This feature facilitates a less abrupt transition between different brightness levels, such as from 50% on to 100% on.

In an exemplary implementation of an occupancy sensor according to the present invention, any one, or combination, of the following feature can be implemented:

Immunity to false tripping—radiated and conducted RFI
Zero Cross Switching on both close and open
Manual ON switch SW (only way lights turn ON—except during Grace Time)
Auto ON option for turning the lights on automatically anytime an occupant enters occupancy sensor field of view (FOV). The FPS works as an on/off override
50% dim down for 30 seconds before lights off, for example if load is at 100% dim to 50%, if load is 50% dim to 25%.
Soft start: this feature ramps the light level up or down anytime it's changed (for example, soft start time=2 seconds)—can be implemented to work for 50% dim down feature
standard US Mounting Height: 42" to 54"
North American Box Mounting
120V 60 Hz
Loads: 400-500 Watts Incandescent; Min Load: 40-50 Watts Incandescent; "0" HP required
Sensor Field of View:
  1. Operate in a 12×20 Room
  2. NEMA WD-7 Occupancy Motion Sensors—½ Scale Coverage
     Distance; 150° Field of View
Light Adjustment:
  1. Not used in manual on.
  2. Used in auto on sensors. Daylight set push button to set calibration, lights off, average readings over 30 sec. Offset to leave lights off after calibration. Next time occupant enters read photocell check if ambient>calibrated level=leave light off, else, if<calibrated level=switch light on. Photocell is checked~1×/min. if lights are off. Lights never switch off while occupant in area based on photocell.

Time Adjustment: Test (30 sec), 10, 20, 30 minutes
Line/Load/Ground wires marked (no neutral needed to operate)
Green indicator LED flashes when sensing motion
Night light
FCC Part 15 Subpart B Class A Compliant
Metal Strap
Airgap off switch
IPC Class 2
Dimming control: Vertical dial next to "Manual On" switch
Dim control range: 10% to 100% light intensity. 10% low-end limit prevents off or zero dimming mode=energy waste
Dim preset on/off control: Dim preset level is controlled by the dial and switched on/off via Manual On SW. (Light level goes to whatever level the dial is set too, and is switched on or off via the Manual On SW)
Operating Temp. Range: 0° C. to 50° C.
Storage Temp. Range: −10° C. to +85° C.
Relative Humidity Range: 20% to 90% non condensing
Withstand cold (~18° C.) drop test from 3 feet from all axis in box on a hardwood floor
Voltage range performance: −10% to +10%
Electrostatic Discharge (ESD) protected
Fast transient burst/surge
Safe short circuit protection—Line to Neutral or lamp failure FIGS. 6A and 6B show schematics of a front and side view of a front panel 610 of an occupancy sensor according to an exemplary embodiment of the present invention. As shown in FIGS. 6A and 6B, PIR lens 516 is mounded in portions 612 of the front panel, LED indicator 616 is mounted through the opening 618 of the front panel (FIGS. 6C and 6D), and body 620 of FPS 600 includes a gap 622 foe accommodating a slide pot (see FIG. 5A) therethrough.

An example of a wall mounted passive infrared occupancy sensor in accordance with another embodiment of the present invention is illustrates in FIGS. 7A through 7D where an occupancy sensor comprises housing 710 and front panel 712 secured to housing 710 by means of, for example, screws 714. Passive infrared (PIR) lens 718 is mounted in part 716, which also includes a front press switch (FPS) 722. In contrast to an embodiment illustrated in FIGS. 5A and 5B. manual dimming control is omitted. An occupancy detection indicator can be provided by means of an LED 720.

Figure 8B:
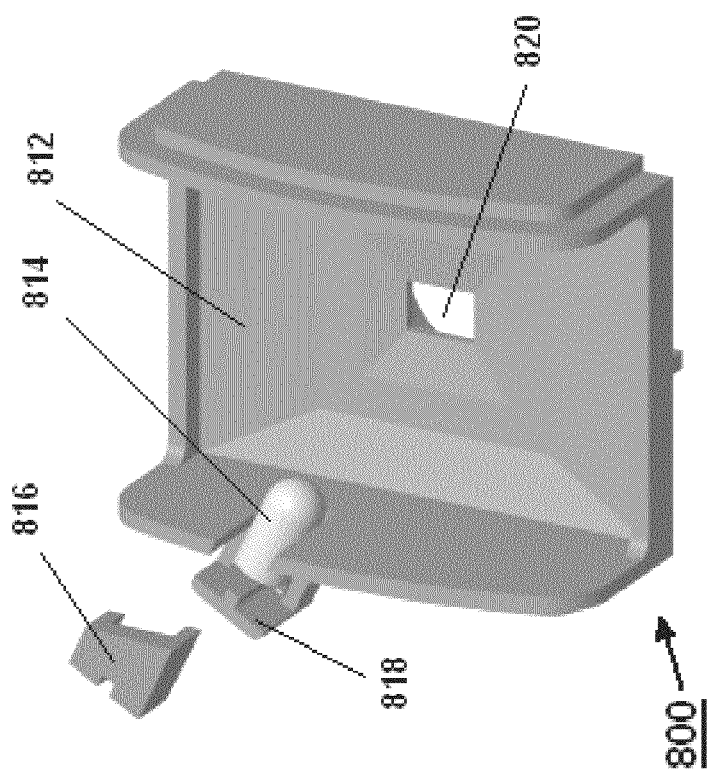
FIGS. 8A and 8B illustrate an exemplary implementation of a night light feature according to certain exemplary embodiments of the present invention
Figure 8A:
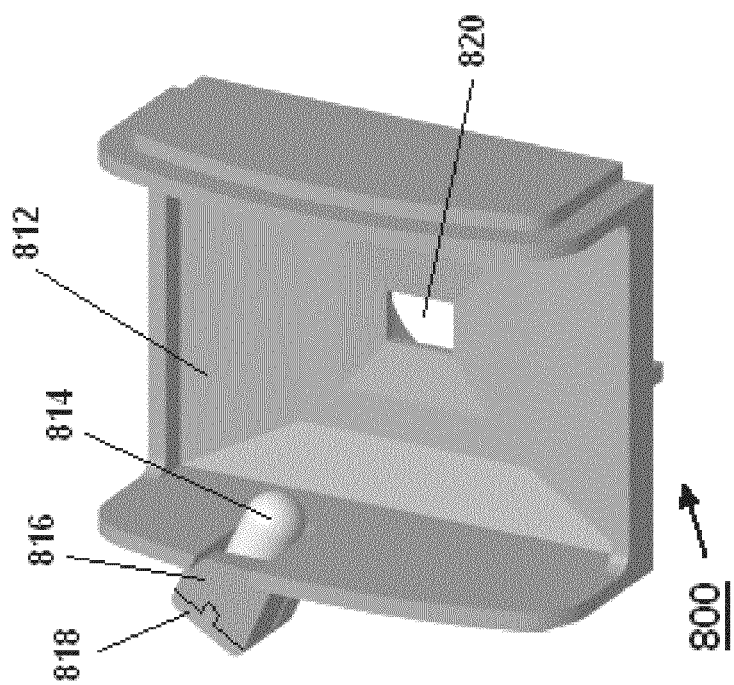

According to another exemplary embodiment of the present invention, a night light feature can be provided in occupancy sensors described above. An exemplary implementation of a night light is illustrated in FIGS. 8A and 8B where night light 800 is positioned with housing 812 of a PIR (not shown) and behind the PIR lens (not shown). Opening 810 for the PIR is provide in housing 812. This exemplary implementation provides LED 814 which can function as a night light (or as an indicator, as described for example in U.S. Pat. No. 5,669,243) and can be removably secured though an opening in a aside of housing 812 by means of a mounting platform 818 and a clip 816. The LED can be configured to illuminate the lens area any time the sensor's load is off. In an exemplary implementation, LED can be selected to operate only if there is insufficient ambient light by use of, for example, photocell control. LED light can emit any suitable color of light, for example, white, amber, green, red, and so on. In yet another exemplary implementation, LED night light can be mounted through the housing to produce a more direct/brighter light.

Exemplary implementations of a system and method incorporating a warning dimming function according to certain embodiment of the present invention are as follows.

Figure 1B:
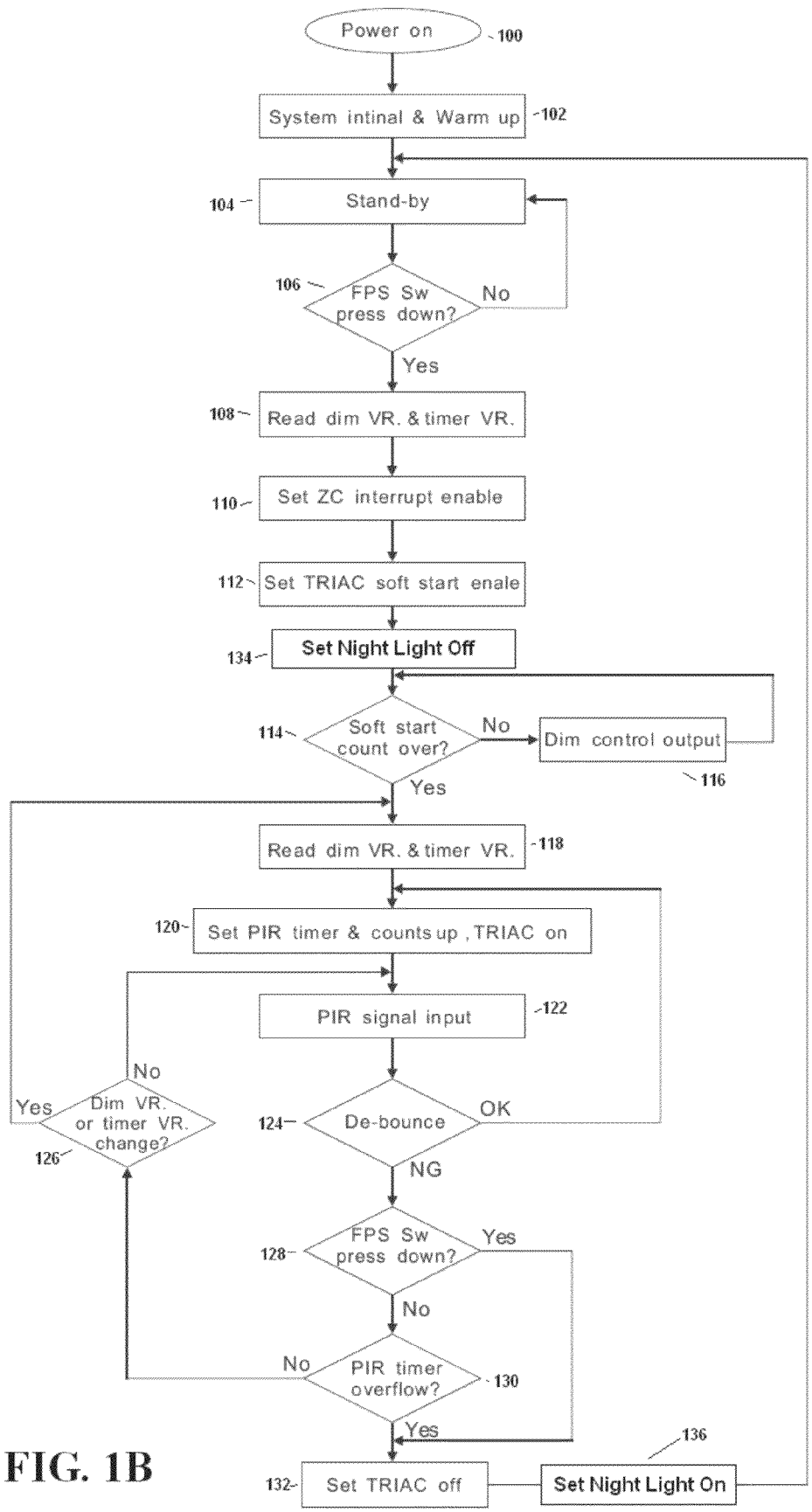
FIG. 1B shows an operational flowchart of system according to another exemplary embodiment of the present invention.
Figure 2A:
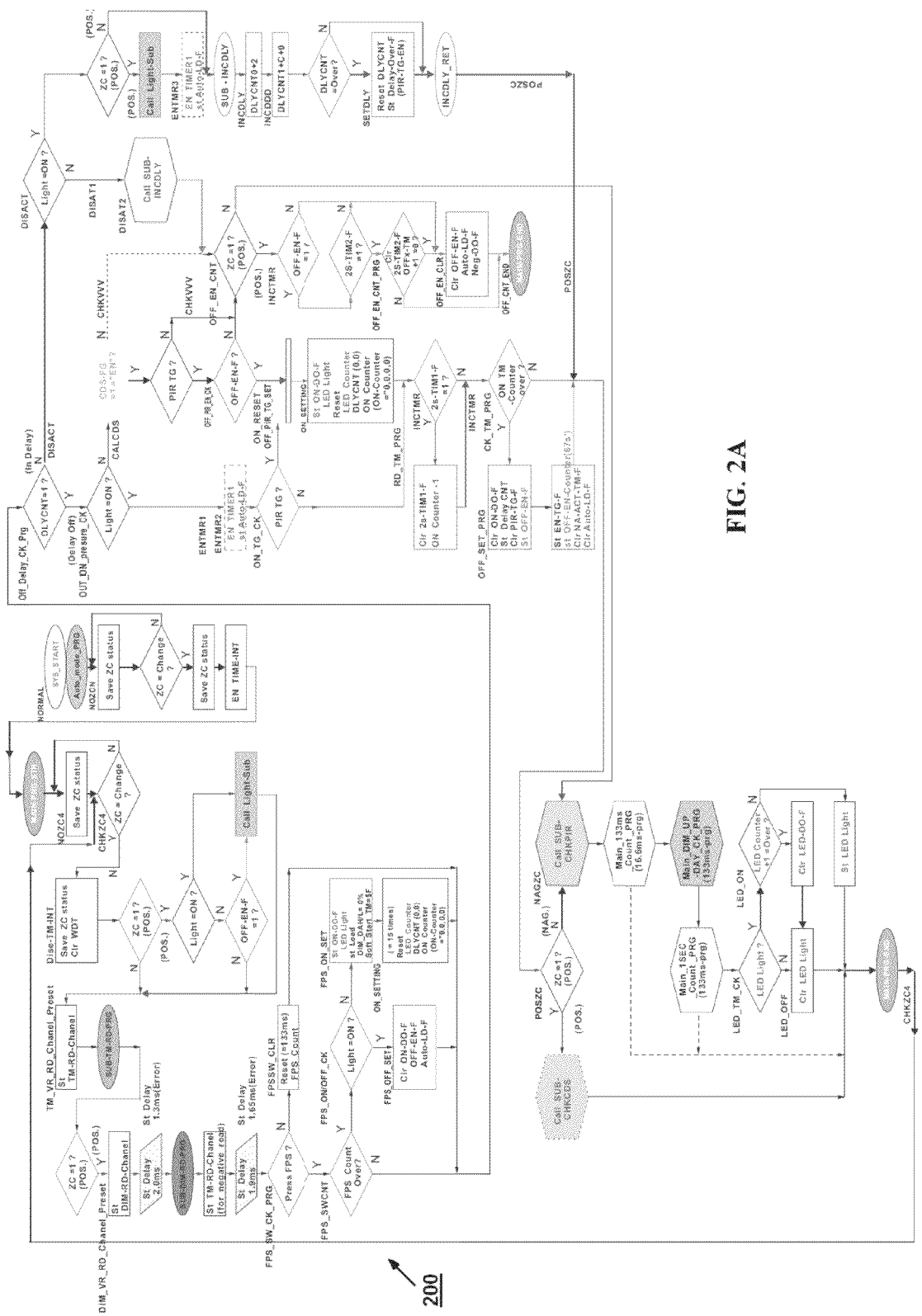
FIGS. 2A-2D show an example of an implementation of an embodiment of the present invention as a set of computer executable instructions.
Figure 2B:
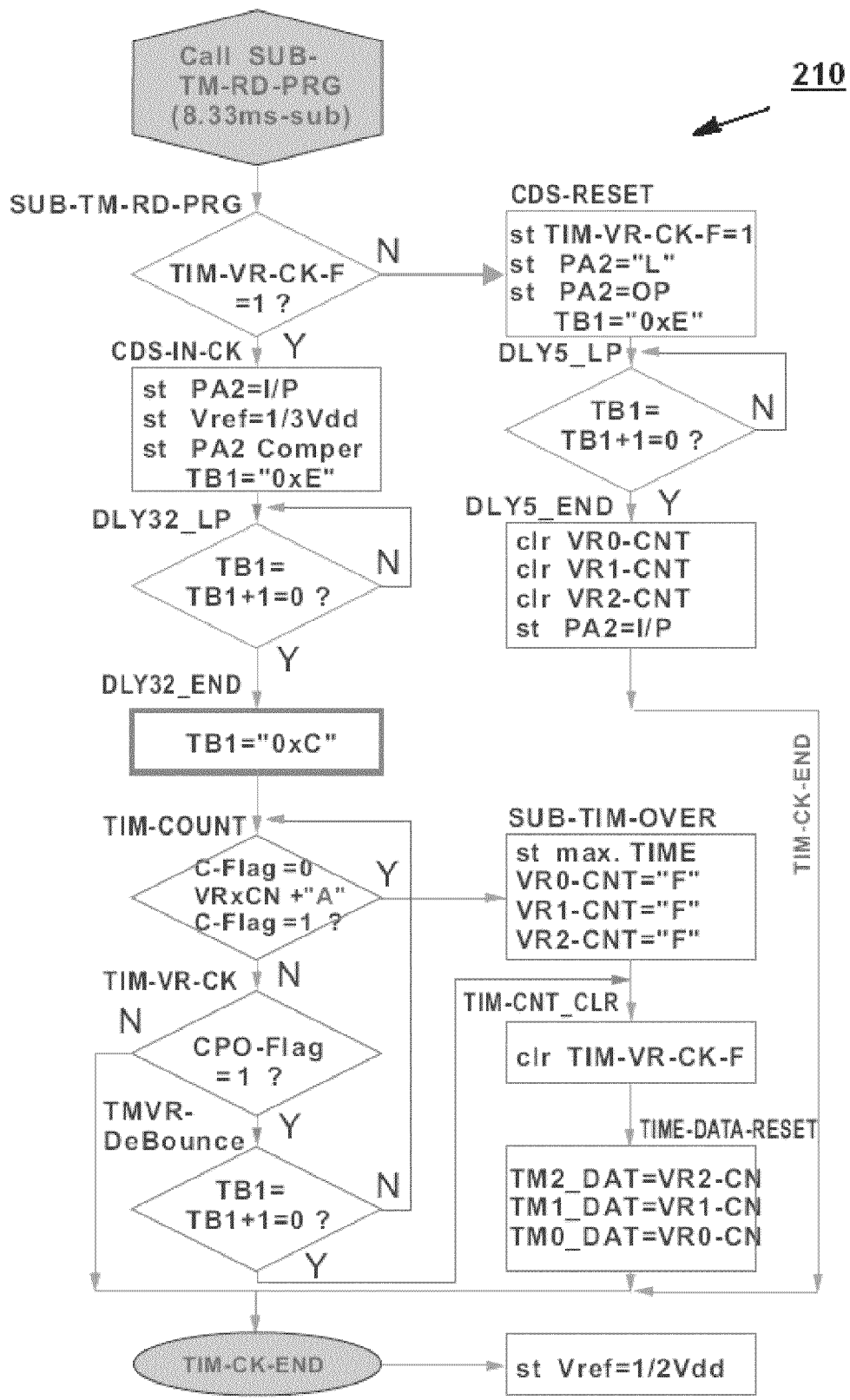
Figure 2C:
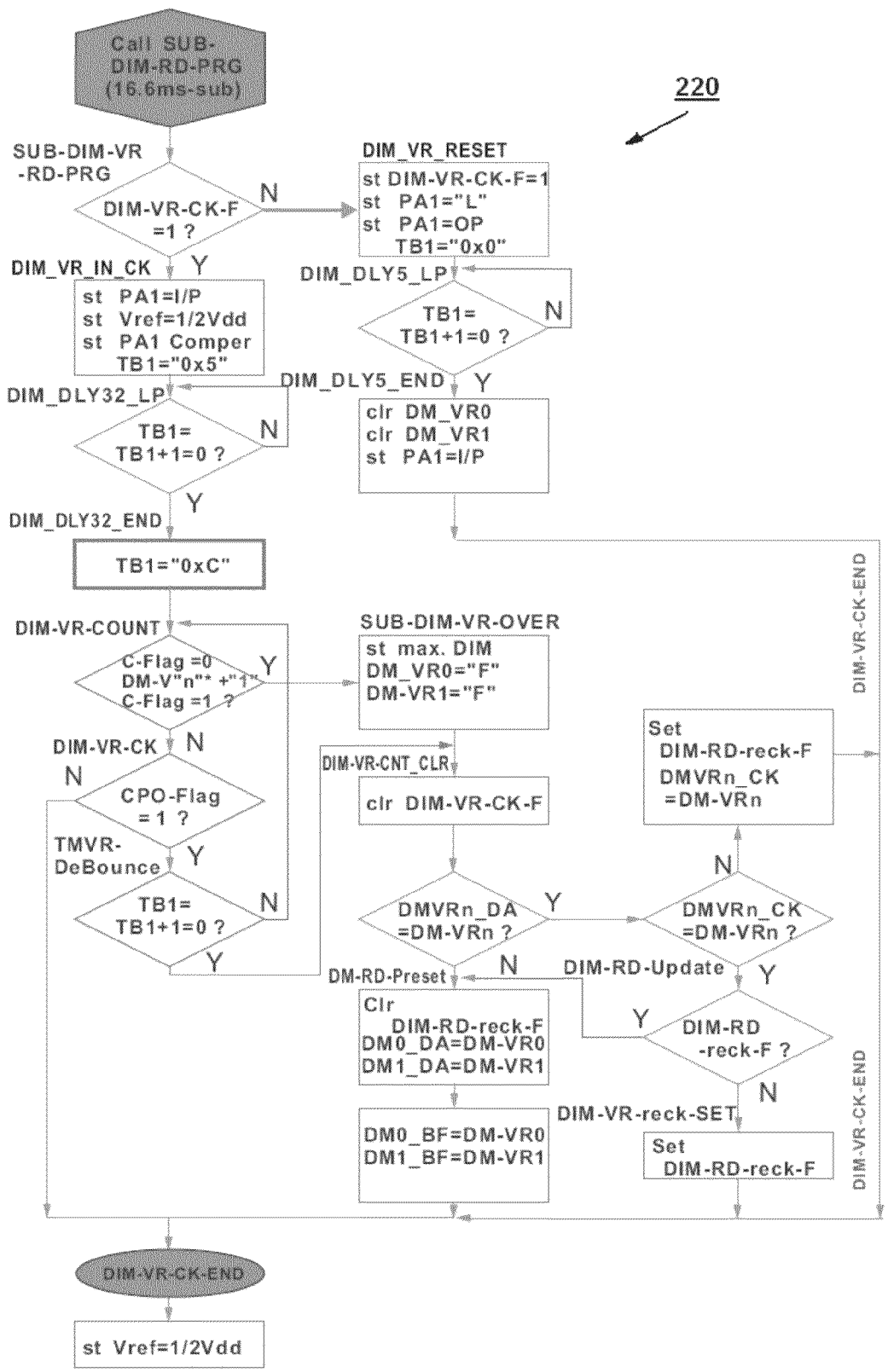
Figure 2D:
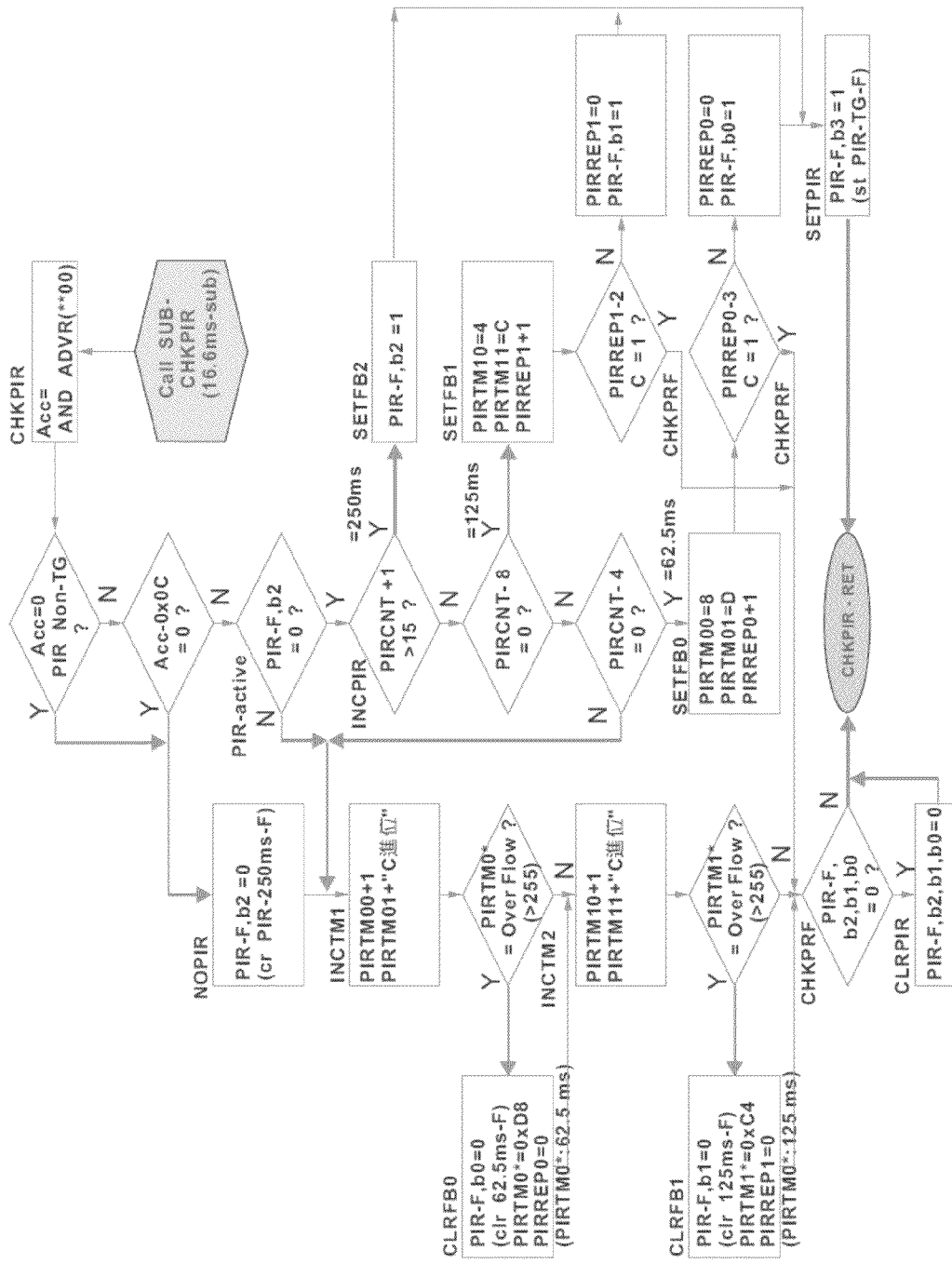

Referring to FIGS. 1A and 1B, after initial power on 100, system initialization and warm up 102 take place, after which stand-by mode 104 is maintained until a manual operating switch, for example a front press switch (FPS) has been pressed down. If it is determined 106 that FPS has been pressed down, values of the voltage regulators (for example, variable resistors) VR of the dimmer and timer circuits (see circuit diagram of FIG. 4) are read 108, ZC interrupt enable is set 110, and a soft start enabled is set 112, provided for example is a TRIode for Alternating Current (TRIAC). If soft start count is not over, dim control output is performed 116. After the soft start count is over, values of dimmer VR and timer VR are read 118, PIR timer is set and counts up, and the TRIAC is on 120. PIR signal output is detected 122. On de-bounce "OK", the operation is returned to step 118, otherwise a determination is made whether FPS is pressed down 128. If FPS is pressed down 128, the TRIAC is set to off 132 and operation return back to standby 104. Otherwise, PIR timer overflow is checked 130 before setting TRIAC to off 132. If PIR timer overflow is confirmed then a determination is made on the change of dimmer VR and timer VR 126. If change has occurred, operation returns to step 118, otherwise operation returns to step 122.

In an exemplary implantation of FIG. 1B, steps for tuning on and turning off nightlight are added whereby the night light is set to off after step 134 and set to on after step 132.

Referring to FIGS. 2A through 2D, an exemplary implementation of the methods described in, for example, FIG. 1A in a software program are illustrated by means of logic flow charts 200, 210, 220 and 230 which can be programmed for example in an ASIC.

Figure 3A:
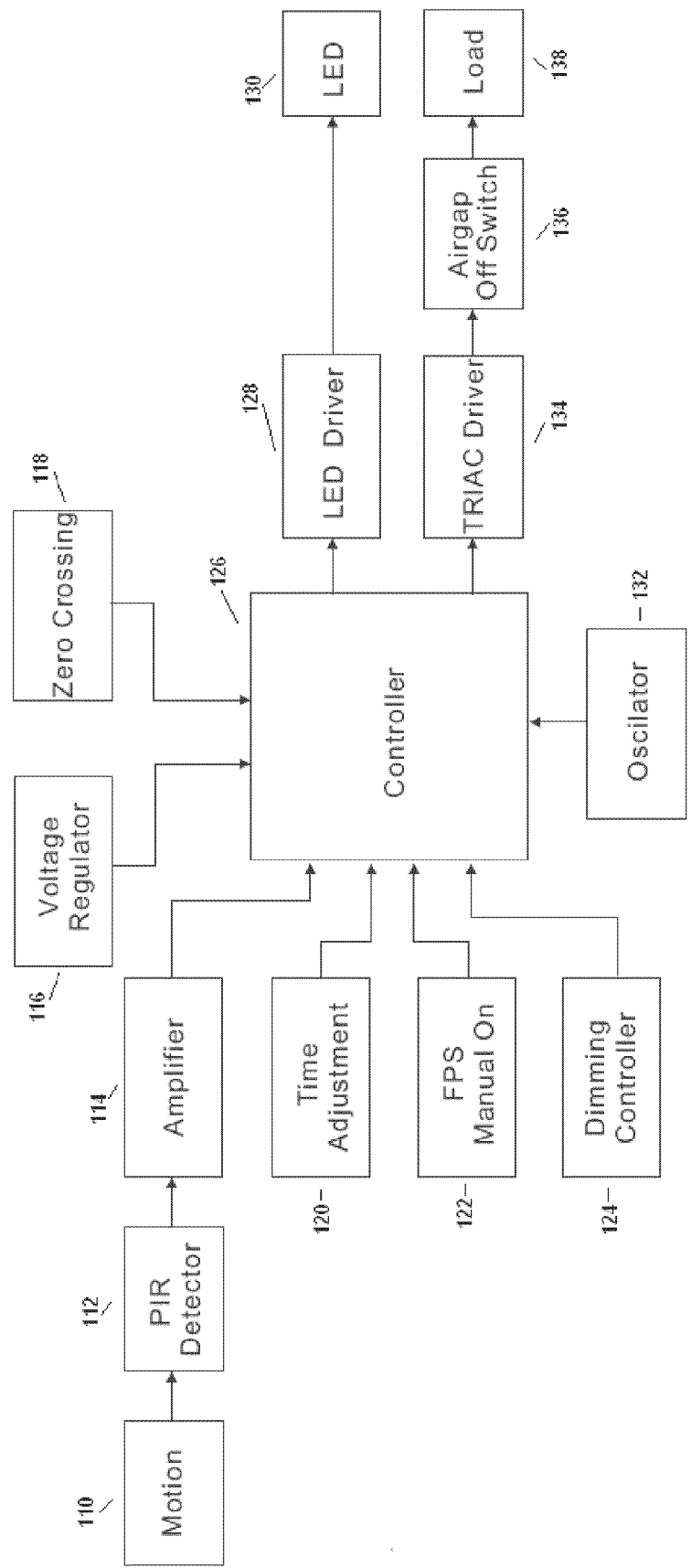
FIG. 3A is a block diagram of a system according to an exemplary embodiment of the present invention.
Figure 3B:
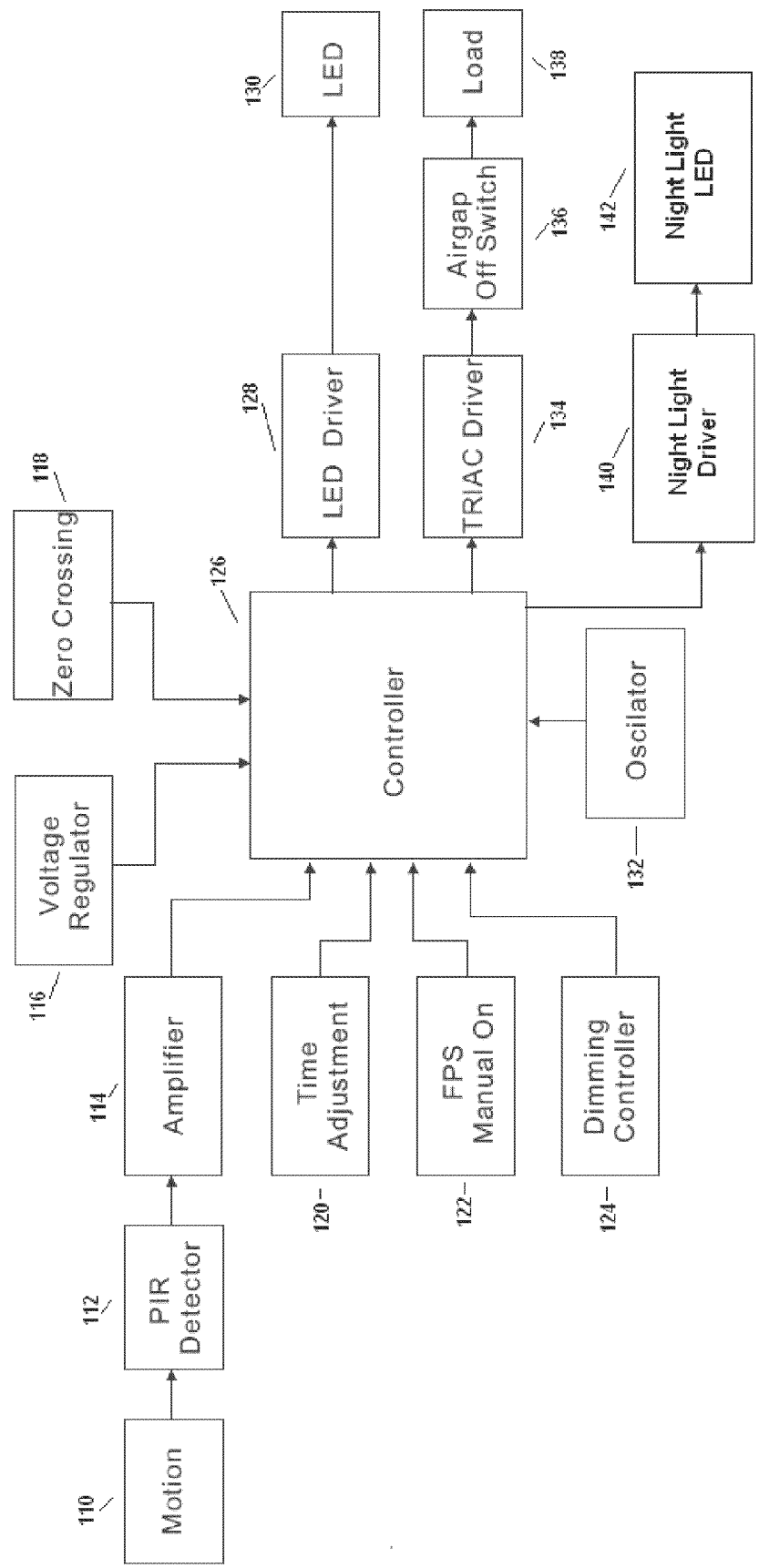
FIG. 3B is a block diagram of a system according to another exemplary embodiment of the present invention.

Referring to FIGS. 3A and 3B, block diagrams of systems according to exemplary embodiments of the present invention are provided where an occupancy sensor comprises a controller 126 having coupled thereto: an amplifier 114 which receives signals from PIR detector 112 coupled to motion sensor 110; voltage regulator 116; zero crossing circuit 118; time adjustment circuit 120; FPS manual on switch 122; dimming controller 124; oscillator 132; LED driver 128 for driving LED 130; and TRAC driver 134 connected to load 138 via an airgap off switch 136.

In an exemplary embodiment of FIG. 3A, a night light driver 140 for driving nightlight 142 are also coupled to controller 126.

Figure 4:
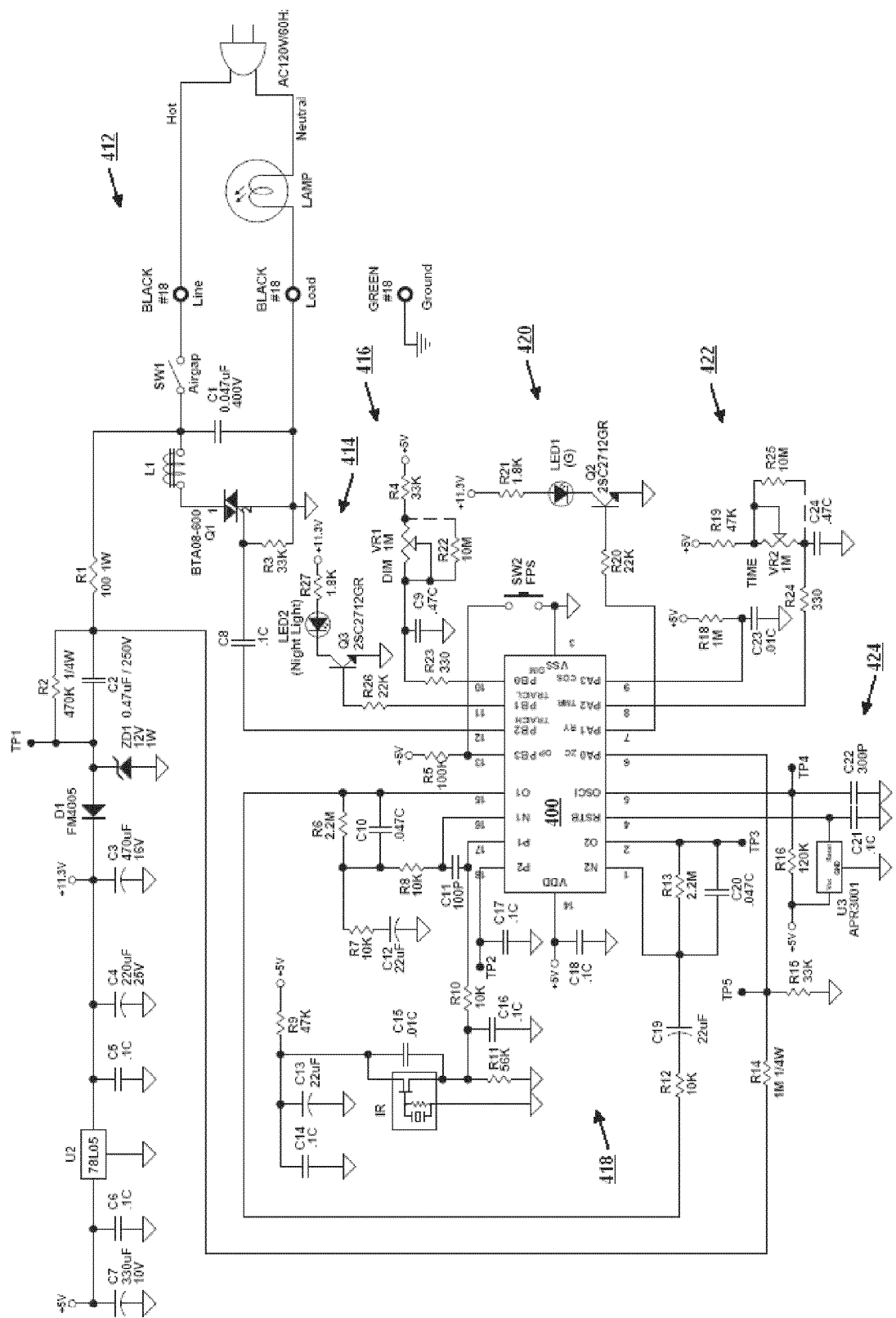
FIG. 4 is a circuit diagram of a system according to an exemplary embodiment of the present invention.

FIG. 4 is an example of a circuit design implementing the features illustrated in block diagrams of FIGS. 3A and 3B as described above with reference to FIGS. 1A and 1B, including night light circuitry 414, LED indicator circuitry 420; timer circuitry 422; TRIAC driver circuitry 412; and a controller implemented by means of a programmable microprocessor 400.

Numerous additional modifications and variations of the present invention are possible in light of the above teachings. It is therefore to be understood that within the scope of the appended claims, the present invention may be practiced otherwise than as specifically described herein.

We claim:

1. A light control system comprising:
    a sensor for detecting an occupancy in an area;
    a timer for determining if the occupancy is not detected by the occupancy sensor before a first time period expires;
    a dimmer for changing a light level in said area from a first light level to a second light level when determining that a second time period after the occupancy is not detected is remaining on the timer before the first time period expires, and for changing said light level in said area from the second light level to a third light level when determining that the first time period expired and the occupancy is not detected during the second time period; and
    a controller coupled to the sensor, the timer and the dimmer to control the light level
    to remain at the second light level until the first time period expires if the occupancy sensor does not detect occupancy during the second time period,
    change to the first light level from the second light level, and reset the timer to the first time period, if the occupancy sensor detects occupancy during the second time period, and
    change to a third light level from the second light level, when the first time period expires if the occupancy sensor does not detect occupancy during the second time period;
    wherein:
    the second light level is not equal to the first light level; and
    the third light level is not equal to the second light level.

2. The light control system of claim 1, wherein the second light level is lower than the first light level.

3. The light control system of claim 1, wherein the third light level is lower than the first light level.

4. The light control system of claim 1, wherein at least one of the first and second time periods comprises at least one of a variable and preset time period.

5. The light control system of claim 1, wherein at least one of the first, second and third light levels comprises at least one of a variable and preset level.

6. The light control system of claim 1, further comprising a night light.

7. The light control system of claim 6, wherein the night light comprises a light emitting diode (LED).

8. The light control system of claim 6, wherein the night light is configure to be on when the lights source is off and to be off when the light source is on.

9. The light control system of claim 6, further comprising a photocell configured to detect ambient light whereby at least the first light level is adjusted based on the detected ambient light.

10. The light control system of claim 1, further comprising a light source connected to the dimmer and outputting light at the light level
    wherein if the occupancy sensor detects occupancy during the second time period, the controller controls the light level to gradually change from the second light level to the first light level over a fourth time period
    wherein the changing to the first light level if the occupancy sensor detects occupancy during the second time period comprises gradual change to the first light level from the second light level over a fourth time period.

11. A method of controlling light output, the method comprising:
    detecting an occupancy in an area;
    determining if the occupancy is not detected in the area before a first time period expires on a timer;
    determining if a second time period after the occupancy is not detected is remaining on the timer before the first time period expires;
    changing a light level in said area from a first light level to a second light level when determining that the second time period after the occupancy is not detected is remaining on the timer before the first time period expires;

controlling the light level to remain at the second light level until the first time period expires if the occupancy sensor does not detect occupancy during the second time period;

changing the light level to the first light level from the second light level, and resetting the timer to the first time period, if the occupancy sensor detects occupancy during the second time period; and changing the light level to a third light level from the second light level, when the first time period expires if the occupancy sensor does not detect occupancy during the second time period, wherein the second light level is not equal to the first light level, and the third light level is not equal to the second light level.

12. The method of claim 11, further comprising:
turning on a night light if a light source is off; and
turning off the night light if the light source is on.

13. The method of claim 12, wherein the night light comprises a light emitting diode (LED).

14. The method of claim 11, wherein the second light level is lower than the first light level.

15. The method of claim 11, wherein the third light level is lower than the first light level.

16. The method of claim 11, wherein at least one of the first and second time periods comprises at least one of a variable and preset time period.

17. The method of claim 10, wherein at least one of the first, second and third light levels comprises at least one of a variable and preset level.

18. The method of claim 11, further comprising:
detecting ambient light; and
adjusting at least the first light level based on the detected ambient light.

19. The method of claim 11, further comprising configuring a light source to output light at the light level, wherein the changing the light level to the first light level if the occupancy sensor detects occupancy during the second time period comprises gradually changing the output light from the second light level to the first light level over a fourth time period.

20. A non-transitory computer readable medium for storing thereon a set of computer executable instructions comprising:
a first set of instruction for detecting an occupancy in an area;
a second set of instructions for determining if the occupancy is not detected in the area before a first time period expires on a timer;
a third set of instructions for determining if a second time period after the occupancy is not detected is remaining on the timer before the first time period expires;
a fourth set of instruction for changing a light level in said area from a first light level to a second light level when determining that the second time period after the occupancy is not detected is remaining before the first time period expires;
a fifth set of instruction for controlling the light level to remain at the second light level until the first time period expires if the occupancy sensor does not detect occupancy during the second time period;
a sixth set of instruction for changing the light level to the first light level from the second light level, and resetting the timer to the first time period, if the occupancy sensor detects occupancy during the second time period; and
a seventh set of instructions for changing the light level to a third light level from the second light level, when the first time period expires if the occupancy sensor does not detect occupancy during the second time period,
wherein the second light level is not equal to the first light level, and the third light level is not equal to the second light level.

* * * * *